United States Patent [19]

Spagnoli et al.

[11] Patent Number: 5,653,982
[45] Date of Patent: Aug. 5, 1997

[54] COSMETIC OR DERMATOLOGICAL COMPOSITIONS CONTAINING RIBOSOMES

[75] Inventors: Roberto Spagnoli; Margaret Varkados, both of Paris, France

[73] Assignee: The Boots Company PLC, Nottingham, England

[21] Appl. No.: 442,008

[22] Filed: May 16, 1995

Related U.S. Application Data

[63] Continuation of Ser. No. 257,545, Jun. 9, 1994, abandoned.

[30] Foreign Application Priority Data

Jul. 2, 1993 [FR] France .................... 93 08110

[51] Int. Cl.$^6$ .................................................. A61K 35/74
[52] U.S. Cl. .................. 424/195; 514/8; 514/44
[58] Field of Search .............. 424/195.1; 435/255, 435/256, 259, 270; 530/821, 824; 514/8, 44

[56] References Cited

U.S. PATENT DOCUMENTS

| 4,540,571 | 9/1985 | Schimanski | 424/81 |
| 5,019,391 | 5/1991 | Bunte et al. | 424/195.1 |

OTHER PUBLICATIONS

Van de Graaf & Fox, Concepts in Human Anatomy & Physiology, WC Brown, Dubuque, Iowa 1986.

*Primary Examiner*—Jean C. Witz
*Attorney, Agent, or Firm*—Nikaido, Marmelstein, Murray & Oram LLP

[57] ABSTRACT

Cosmetic or dermatological compositions for skin care, characterized in that they contain ribosomes extracted from vegetable or animal cells or from the cells of microorganisms.

14 Claims, 1 Drawing Sheet

COSMETIC OR DERMATOLOGICAL COMPOSITIONS CONTAINING RIBOSOMES

PRIOR APPLICATION

This application is a continuation of U.S. patent application Ser. No. 257,545 filed Jun. 9, 1994, now abandoned.

The present invention relates to new cosmetic or dermatological compositions for skin care, characterized in that they contain ribosomes extracted from vegetable or animal cells or from the cells of microorganisms. These new compositions are intended in particular to delay the signs of aging of the skin.

BACKGROUND OF THE INVENTION

As aging of the skin progresses, changes take place, particularly at the epidermal and dermal levels. Within the epidermis, the production of new cells no longer compensates for desquamation, and the epidermis gradually gets thinner. The sebaceous glands become functionally less active and the skin becomes dry.

At the level of the dermis, the formation of new collagen, responsible for skin tone, is slowed by reduction of the secretive activity of the fibroblasts. Intermolecular crosslinks within the collagen fibers multiply, bringing about structural rigidity, reduction in the capacity to absorb water, and reduction in the supply of nutrients and oxygen.

These harmful transformations cause a loss of elasticity, as well as dehydration, asphyxiation, and dryness of the skin. These phenomena produce wrinkles, notably on the face where the skin is under particular attack by external factors (e.g. bad weather, pollution, light radiation) and by internal factors (illnesses, increase in age, etc).

Cosmetic preparations intended to combat aging of the skin already exist on the market. These known preparations contain many varied compounds, such as biologicals (for example placenta extracts), collagen, polyvitamin mixtures, and essential fatty acids. Cosmetic compositions containing fetal calf serum, extracts from organs such as the thymus or spleen, and animal extracts are also known, described for example in French Patent Application 84 19446.

However the use in beauty care of the real topical properties of ribosomes has never before been described, and ribosomes extracted from vegetable and animal cells, or from the cells of microorganisms, have never before been used to combat aging of the skin. Ribosomes are the sub-cellular organelles composed of RNA and proteins involved in the synthesis of proteins. By way of illustration, it can be noted that the ribosomes of E. coli (gram negative) consist of the fractions:

70 S (M: $2.7 \times 10^6$ dalton)

50 S (M: $1.8 \times 10^6$ dalton)

30 S (M: $0.91 \times 10^6$ dalton)

The fractions 50 S and 30 S themselves have the following composition:

50 S: 34 proteins, 2RNA (23 S, 5S)

30 S: 21 proteins, 1RNA (16 S).

SUMMARY OF THE INVENTION

The present invention is based on the discovery that these ribosomes possess remarkable stimulating and regenerating power and, in particular, they possess a stimulating effect on cellular growth. These various properties can be advantageously used in dermatology and in beauty care.

One of the advantages of compositions of the present invention have over the known compositions of the prior art is that, by replacing the fetal calf serum with ribosomes extracted from vegetable or animal cells or from cells of microorganisms, risks of viral infection can be avoided. These include risks of infection by prions, which are new infectious agents which began to appear in the middle of the 1980's and are responsible for the so-called epidemic of mad cow disease or bovine spongiform encephalitis. On the other hand, the identity of the strains or, in general, the cells, from which the ribosomes are extracted is easy to verify on a permanent basis. This ensures that the extract employed can be perfectly reproduced both from the point of view of its genetic origin and its composition.

BRIEF DESCRIPTION OF DRAWINGS

In the accompanying drawings, constituting a part hereof.

DETAILED DESCRIPTION OF THE INVENTION

Figure 1:
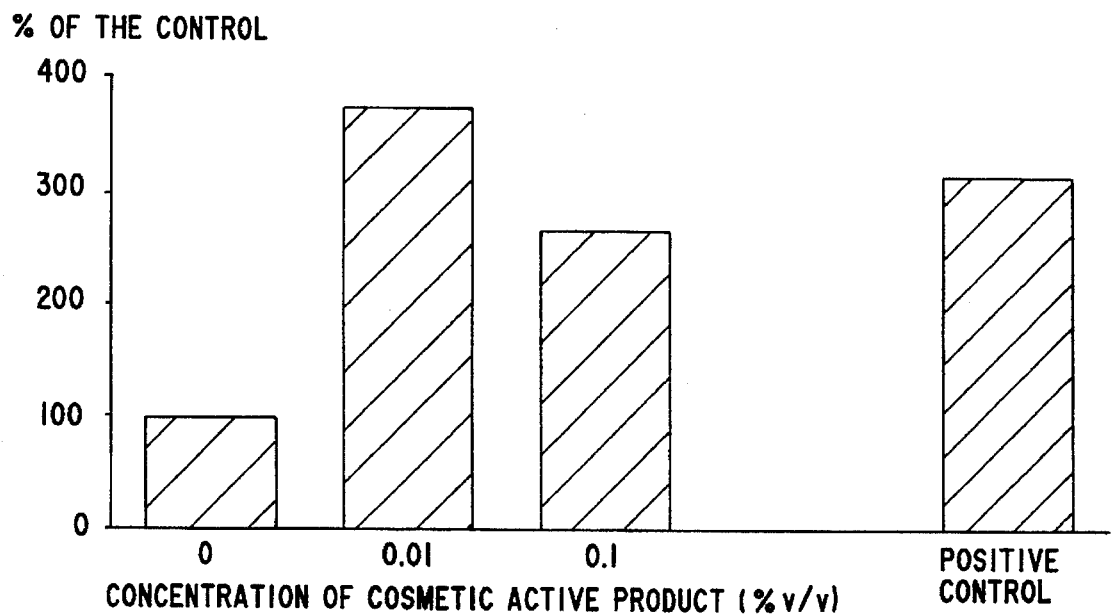
FIG. 1 is a bar graph showing the results of the tests of neosynthesis of proteins.

The present invention relates in particular to cosmetic or dermatological compositions characterized in that the ribosomes are extracted from eukaryotic or prokaryotic microorganisms, gram negative bacteria from the group *Klebsiella pneumoniae*, Hafnia, *Escherichia coli, Klebsiella ozoenae, Enterobacter chloacae, Pseudomonas aeruginosa*, and Proteus. This can also be extracted from gram positive bacteria such as *Bacillus subtills*, Arthrobacter sp., Lactobacillus, or Staphylococcus (particularly, *Staphylococcus aureus*). Among the ribosomes extracted from gram negative bacteria, those extracted from the group *Klebsiella pneumoniae*, Hafnia, or *Escherichia coli* are preferred. Compositions made therefrom are, of course, also particularly preferred.

Among the ribosomes extracted from *Klebsiella pneumoniae*, those extracted from the *Klebsiella pneumoniae* strain deposited at the Pasteur Institute in Paris under number I-163 are worthy of special mention. As to the ribosomes extracted from Hafnia, those extracted from the Hernia strain deposited at the Pasteur Institute in Paris under number I-868 are of particular value. Among the ribosomes extracted from Escherichia coli, those extracted from the Escherichia coli strain deposited at the Pasteur Institute in Paris under number I-870 or the MRE600 strain from the Microbiological Research Establishment, Salisbury, England are also to be preferred. In the compositions of the invention, the ribosome extract can be used in powdered form or in the form of an aqueous suspension.

The invention relates especially to cosmetic and dermatological compositions containing $5 \times 10^{-5}$% to 1%, preferably 0.005% to 0.05%, by weight of a suspension of ribosomes extracted from vegetable or animal cells, or from cells of microorganisms. A most preferred form of the invention contains about 0.01% by weight of the suspension of ribosomes. The ribosomes can be prepared according to the usual methods known to those of ordinary skill in the art.

The present invention also relates to the preparation of ribosomes extracted from vegetable or animal cells, or from the cells of microorganisms. In an advantageous form of the invention, the ribosomes extracted from microorganisms are prepared according to the following successive stages:

(1) culture of the microorganism strain on a liquid or solid medium, (2) collection after complete development of the microorganisms, (3) lysis of the microorganisms, and (4) treatment of this lysate by centrifuging, precipitation with ammonium sulphate, centrifuging again, molecular sieving, precipitation with PEG 6000, centrifuging once more, and dialysis of the solution obtained.

The media on which the microorganisms can be cultured are the usual and inexpensive liquid or solid media including a carbon source, a natural or inorganic source of nitrogen, and mineral salts, such as are well known to one skilled in the art. The literature gives many examples of such culture media. There can be mentioned, for example, chapter 1.6 "Culture Media" of the book "Biochemical Engineering and Biotechnology Handbook", 2nd Edition 1991 (Stockton Press).

After collection, the microorganisms are taken up in a buffer such as the polymix I buffer which contains:

| | | |
|---|---|---|
| $MgCl_2$ | 5 mM | pH = 7.5 |
| $CaCl_2$ | 0.5 mM | |
| Putrescine | 8 mM | |
| Spermidine | 1 mM | |
| Tricine | 20 mM | |
| $NH_4Cl$ | 5 mM | |
| KCl | 95 mM | |
| DTT | 1 mM | | the buffer may also include:

| | | |
|---|---|---|
| Tris/HCl | 20 mM | pH = 7.6 |
| $NH_4Cl$ | 100 mM | |
| $Mg(OAc)_2$ | 10 mM | |

The lysis of the microorganisms is then carried out, for example, at high pressure or by grinding with alumina.

Then the lysate obtained is centrifuged at approximately 10,000 to 13,000 rpm, the proteins are precipitated (preferably with ammonium sulphate) at a concentration of 210 mg/ml, and the pH is adjusted to 7.5. After another centrifugation, then molecular sieving, and followed by elution in polymix II buffer;

| | | |
|---|---|---|
| $MgCl_2$ | 5 mM | pH = 7.5 |
| $CaCl_2$ | 0.5 mM | |
| Putrescine | 8 mM | |
| Spermidine | 1 mM | |
| Tricine | 20 mM | |
| $NH_4Cl$ | 150 mM | |
| KCl | 95 mM | |
| DTT | 1 mM | | the fraction containing the ribosomes is precipitated, preferably with PEG 6000 at 100 mg/ml.

After centrifuging again, the solution obtained is dialysed for about one night in a buffer such as Tris/HCl

| | | |
|---|---|---|
| | 20 mM | |
| $NH_4Cl$ | 60 mM | |
| $Mg(OAc)_2$ | 10 mM | pH = 7.6 |

In this way the desired ribosomes are obtained. It should be noted that the purification of the ribosomes could be stopped either at the end of the centrifugation after lysis of the microorganism cells, or at the end of centrifugation after the precipitation stage of the proteins with ammonium sulphate.

To date it was known and was usual to use, as the cell growth factor in cell culture in vitro, animal serum (more particularly fetal calf serum), in a concentration of the order of 10%. Also used are synthetic substituents of the serum which are marketed at a high price and the composition of which is kept secret, for example Ultroser HY (IBF), NU-SERUM (Sochibo), and/or individual factors such as the epidermal growth factor "EGF". Ribosomes have never been used for this purpose.

The use of ribosomes as a cell growth factor in vitro is a feature of the present invention. Moreover, they can be used at very low concentrations. Such use is an economically advantageous alternative to the prior art methods.

The stimulating power of the ribosomes according to the invention has been studied in comparison with that of fetal calf serum and epidermal growth factor (EGF), as positive control media, in cultures of keratinocytes of the human epidermis. An example of one such study, which shows the superiority of the stimulating power on cell growth of the ribosomes over known and commonly used compounds (fetal calf serum and EGF) is described hereafter. The present invention, therefore, also is directed to the use of ribosomes extracted from microorganisms as a growth factor for the culture of keratinocytes in vitro.

Furthermore, by studying the activity of the ribosomes of the present Application, it was observed that they showed a remarkable inducing activity like that of EGF, without having the toxicity of the latter. Therefore the ribosomes can be used to facilitate the regeneration of the skin and the epidermis. The skin-regenerating properties resulting from stimulation of cell growth by the compositions according to the invention endow them with surprising effectiveness in combating aging of the skin. The usual dose, variable according to the product used, the subject being treated, and the illness in question, can be, for example, from 50 mcg to 5 mg per day by local application for man.

Particular subjects of the invention are cosmetic and/or dermatological compositions in the form of liquid or solid preparations for topical use. They are preferably presented in one of the following forms:

aqueous gels, fatty gels, simple water-in-oil emulsions, simple oil-in-water emulsions, multiple emulsions, e.g.:

water-in-oil-in-water or oil-in-water-in-oil, triple water-in-oil-in-water, triple oil-in-water-in-oil, oil-in-water containing liquid crystals, complex emulsions containing liquid crystals forming lipid double, layers surrounding the oily phases, pseudo-emulsions (dispersions of an oily phase or a water-in-oil emulsion in a gelatinized aqueous phase, without traditional surfactants), oil-in-water or water-in-oil micro-emulsions, emulsions containing two dispersed oil phases, different from, and insoluble in, each other, a pseudo-emulsion or dispersion of an oily phase dispersed in an aqueous phase and stabilized with Lubragel®, Pemulen®, Hypan®, xanthan gum, CMC, hydroxyethyl cellulose, Amigel®, polyvinylpyrrolidone, Amercell HM 1500®, or a mixture of two or more of these gelatinizing agents.

Optionally, the compositions according to the invention may contain filters, screens for solar radiation, vitamin extracts, perfumes, preservatives, anti-oxidants, coloring agents, and the like.

The corresponding dermatological compositions can be solid or liquid and in the dermatological forms commonly used, such as creams, gels, ointments, lotions, milks for the skin, drops, eyelotions, aerosols, shampoos, or in the form of liposomes; they are prepared according to the usual methods. The active ingredient or ingredients can be incorporated with excipients usually employed in these pharmaceutical compositions, such as talc, gum arabic, lactose, starch, magnesium stearate, cocoa butter, aqueous or nonaqueous vehicles, fatty substances of animal or vegetable origin, paraffin derivatives, glycols, wetting, dispersing or emulsifying agents, and preservatives.

The compositions of the invention can contain, in addition to the ribosome extracts, other active compounds having particular skin properties. Therefore the compositions of the invention can also contain oleyl acetate. This product has anti-lipase properties and directly prevents the formation of comedones or blackheads. The compositions thus obtained contain two active constituents which, by their combined action, constitute a product which is well adapted to skins having a tendency toward ache.

The compositions of the invention optionally also contain a compound favoring the healing of lesions caused by ache, such as a Centella Asiatica extract or, more particularly, a titrated dry extract from Centella Asiatica. Other substances such as evening primrose oil, amino acids, can also be incorporated.

The cosmetic compositions according to the invention can be presented in any of the forms used in beauty care i.e.; creams or gels in pots or in tubes, milks, lotions in glass or plastic bottles, dropping bottles, vials, aerosols, etc. Therefore the invention relates to cosmetic compositions, characterized in that they are presented in the form of creams, gels, milks, lotions, emulsions, liquid soaps, dermatological bars, shampoos, or the like.

For each form, suitable excipients can be used. These excipients must have the qualities usually required. They must be endowed with a great affinity for the skin, be perfectly well tolerated, stable, and have an adequate consistency, thereby allowing easy and agreeable use.

As examples of preferred excipients, mention is made of hydrocarbons, silicone fluids, fatty acid triglycerides, synthetic triglycerides, vegetable, animal, or mineral waxes, fatty acids or alcohols, esters of fatty acids or fatty alcohols, fatty acid amides, lanolin, non-ionic surfactants, anionic surfactants, natural or synthetic gelatinizing polysaccharides, deacetylated chitin, cellulose derivatives, guar derivatives, polyols, polyalkyleneglycols, mineral fillers, organic pigments, and organic coloring lacquers. Also advantageous are known and common excipients such as polymers of carboxyvinyl type; polyethyleneglycols; propylene glycol; stearic derivatives such as glycerol stearate; alcohols such as stearyl alcohols, ketostearyl alcohols, cetyl alcohols, and polyoxyethylenated cetyl alcohols; vegetable oils such as avocado oil and sunflower oil; mineral oils such as petroleum oil; glycerine; lanolin derivatives; talc; wetting agents; thickeners; stabilizing agents; emulsifiers; preservatives; perfumes; and coloring agents.

Finally, sunscreens and sun reflectors can be added to these cosmetic compositions to give them protective power against solar radiation. When these additives are insoluble in oily and aqueous phases, they constitute a supplementary phase. They may be chosen, for example, from the following:

perfluoroethers such as FOMBLIN® from the Montecatini Company, insoluble pigments such as:
  titanium oxides
  rutile titanium oxide
  anatase titanium oxide
  pyrogenated titanium oxide such as P 25® from Degussa
  micronized titanium oxide in (SUN VEIL® from Ikeda)
  titanium oxide surface treated with silicones, amino acids, lecithin, or metallic stearates
  iron oxide
  iron oxide surface treated with silicones, amino acids, lecithin, or metallic stearates
  zinc oxide
  micronized zinc oxide such as UFZO® from Cosmo Trends Corporation
  mica covered with titanium oxide.

The different cosmetic forms mentioned above can be obtained according to the usual methods used in this field. The present invention is particularly directed to the compositions as defined above, characterized in that their excipients are suitable for use on the face, neck and hands. The present invention also contemplates the use, as a cosmetic product, of compositions containing ribosomes extracted from microorganisms. The present invention also encompasses a method for the regeneration and the combating of aging of the skin wherein an effective amount of a composition as defined above is applied to the skin.

The examples given below illustrate the invention without limiting it.

EXAMPLE 1

Preparation of Ribosomes

The technique used is derived from that described in the article referenced as follows: JELENC P, Rapid Purification of Highly Active Ribosomes from *Escherichia coli*, Anal Biochem 1980; 105: 369–74. The strain used is *E. coli* MRE600 from Microbiological Research Establishment, Salisbury, England, frozen and stored at −20° C.

The three buffers used are:

| Polymix I buffer: | | |
|---|---|---|
| $MgCl_2$ | 5 mM | pH = 7.5 |
| $CaCl_2$ | 0.5 mM | |
| Putrescine | 8 mM | |
| Spermidine | 1 mM | |
| Tricine | 20 mM | |
| $NH_4Cl$ | 5 mM | |
| KCl | 95 mM | |
| DTT | 1 mM | |
| Polymix II buffer: | | |
| $MgCl_2$ | 5 mM | pH = 7.5 |
| $CaCl_2$ | 0.5 mM | |
| Putrescine | 8 mM | |
| Spermidine | 1 mM | |
| Tricine | 20 mM | |
| $NH_4Cl$ | 150 mM | |
| KCl | 95 mM | |
| DTT | 1 mM | |

-continued

| TRIS buffer: | | |
| --- | --- | --- |
| TRIS HCl | 20 mM | pH = 7.6 |
| NH$_4$Cl | 60 mM | |
| Mg(OAc)$_2$ | 10 mM | |

All the operations are carried out at 4° C. 127 g (net weight) of *E. coli* bacteria is defrosted and taken up in 254 ml of polymix I buffer, followed by lysis of the bacteria by three passages at high pressure yielding a volume of 490 ml, which is then centrifuged for 30 minutes at 13,000 rpm resulting in a volume of 400 ml. This volume is centrifuged for 30 minutes at 13,000 rpm, yielding a volume of 370 ml. OD$_{260}$=112480

The proteins are precipitated with ammonium sulfate (210 mg/ml), and the pH is adjusted to 7.5. The mixture is agitated for 30 minutes resulting in a volume of 395 ml. It is centrifuged for 30 minutes at 13,000 rpm, OD$_{260}$=82855. The supernatant liquid is deposited on SEPHACRYL S 200, pre-balanced and eluted with Polymix II buffer. The fractions which contain the ribosomes are precipitated with PEG 6000 (100 mg/ml), followed by agitation for 30 minutes, centrifugation for 15 minutes at 10,000 rpm, and overnight dialysis against 5 liters of Tris buffer. Expression of the results and calculation methods One unit A$_{260}$ (absorption at 260 nm) corresponds respectively to 24 pmoles/ml of 70S ribosomes, 69 pmoles/ml of 30S sub-unit, and 35 pmoles/ml of 50S sub-unit. The measurements V=44 ml and OD$_{260}$=7620 are therefore obtained, i.e. a suspension containing 2.4 g of 70S ribosomes which, if necessary, undergoes a sterilizing filtration and is then divided into aliquotes, frozen in liquid nitrogen, and stored at −80 C.

EXAMPLE 2

Face Cream

| | |
| --- | --- |
| suspension of ribosomes | 0.5 g |
| oleyl acetate | 2.0 g |
| potassium alkyl phosphate | 2.0 g |
| ethyl hexyl palmitate | 8.0 g |
| hydrogenated lanolin | 5.0 g |
| fatty acid triglycerides | 4.0 g |
| sorbitan stearate | 1.0 g |
| neutralized carboxyvinyl polymer | 0.4 g |
| preservatives | 0.4 g |
| aromatic composition | 0.4 g |
| purified water q.s. to make | 100 g |

EXAMPLE 3

Face Gel

| | |
| --- | --- |
| suspension of ribosomes | 0.5 g |
| Centella Asiatica glycolic extract | 5.0 g |
| propylene glycol | 5.0 g |
| neutralized carboxyvinyl polymer | 0.8 g |
| preservatives | 0.35 g |
| aromatic composition | 0.1 g |
| purified water q.s. to make | 100 g |

EXAMPLE 4

Body Cream

| | |
| --- | --- |
| suspension of ribosomes | 0.2 g |
| glycerol stearate | 4.0 g |
| sorbitan palmitate | 6.0 g |
| perhydrosqualene | 5.0 g |
| diisopropyl-cyclohexane | 7.0 g |
| fatty acid triglycerides | 9.0 g |
| glycerine | 5.0 g |
| preservatives | 0.35 g |
| aromatic composition | 1.0 g |
| purified water q.s. to make | 100 g |

EXAMPLE 5

Face Toning Lotion

| | |
| --- | --- |
| suspension of ribosomes | 0.05 g |
| propylene glycol | 5.0 g |
| preservatives | 0.3 g |
| aromatic composition | 0.1 g |
| ethyl alcohol | 10.0 g |
| purified water q.s. to make | 100 ml |

EXAMPLE 6

Sun Milk

| | |
| --- | --- |
| suspension of ribosomes | 0.1 g |
| sunscreens | 5.0 g |
| vaseline oil | 10.0 g |
| ketearyl octanoate | 9.0 g |
| silicone fluid | 2.5 g |
| P.O.E. cetyl ether | 2.0 g |
| sorbitan stearate | 1.0 g |
| preservatives | 0.35 g |
| aromatic composition | 0.5 g |
| purified water q.s. to make | 100 ml |

EXAMPLE 7

Multiple Emulsion

The following aqueous phase, called the internal aqueous phase, is heated to 80° C.:

| | |
| --- | --- |
| demineralized water | 26.52 g |
| methylparaben | 0.1 g |
| magnesium sulphate | 0.28 g |
| glycerine 30° B | 0.8 g |
| O-cymen-5-ol | 0.04 g |
| The following oily phase is heated separately to 80° C.: | |
| glyceryl isostearate | 2 g |
| polyoxyethylenated hydrogenated ricin oil (7 mols) | 0.2 g |
| capric (caprylic) triglycerides | 8.2 g |
| propylparaben | 0.06 g |
| volatile silicone fluid | 1.6 g |

The aqueous phase is dispersed in the oily phase at 80° C. by agitating vigorously for 5 minutes. The resultant dispersion is cooled slowly to 25° C. This primary water/oil emulsion is then dispersed in the following aqueous phase, called the external aqueous phase, by mixing gently at ambient temperature:

| | |
|---|---|
| lubragel MS ® | 15 g |
| carbopol 980 ® | 0.03 g |
| tetrasodium EDTA | 0.054 g |
| methylparaben | 0.216 g |
| imidazolidinyl urea | 0.216 g |
| pure sodium hydroxide | 0.125 g |
| suspension of ribosomes | 0.5 g |
| demineralized water q.s. to make | 100 g |

EXAMPLE 8

Twin-Phase Emulsion

The following oily phase is heated to 80° C.:

| | |
|---|---|
| stearyl alcohol | 1.0 g |
| cetyl alcohol | 2.0 g |
| ketearyl octanoate | 4.0 g |
| polysorbate 60 | 4.0 g |
| sorbitan stearate | 4.0 g |
| caprylic/capric triglycerides | 3.0 g |
| karite butter | 3.0 g |
| oleyl acetate | 2.0 g |
| silicone fluid | 0.5 g |
| tocopherols | 0.05 g |

The following aqueous phase is heated to 80° C.:

| | |
|---|---|
| carboxy vinyl polymer | 0.3 g |
| preservative | 0.7 g |
| lubragel MS ® | 5 g |
| pure sodium hydroxide | 0.3 g |
| demineralized water q.s. to make | 100 g |

The oily phase is dispersed in the aqueous phase and agitation is carried out vigorously for 10 minutes. The emulsion thus formed is then cooled down slowly to 25° C., the following ingredients are then added to it under moderate agitation:

| | |
|---|---|
| suspension of ribosomes | 0.05 g |
| perfume | 0.2 g |

EXAMPLE 9

Water/Silicone Emulsion

The following oily phase is heated to 60° C.:

| | |
|---|---|
| demineralized water | 73.12 g |
| sodium chloride | 0.8 g |
| pure citric acid | 0.01 g |
| methylparaben | 0.25 g |
| propylene glycol | 2 g |
| O-cymen-5-ol | 0.1 g |

The following silicone phase is heated to 60° C.:

| | |
|---|---|
| isocetyl stearate | 3 g |
| arlacel 83 ® | 0.8 g |
| hydrogenated ricin oil | 0.3 g |
| elfacos ST9 ® | 2.0 g |
| oleyl acetate (anti-lipase) | 0.15 g |

| | |
|---|---|
| silicone DC 3225 ® (DOW CORNING) | 9.0 g |
| volatile silicone | 4.0 g |

The aqueous phase is dispersed in the silicone phase under moderate agitation for 10 minutes. The emulsion thus formed is cooled to 25° C. and the following mixture:

| | |
|---|---|
| suspension of ribosomes | 1 g |
| perfume | 0.3 g | is added under gentle agitation.

EXAMPLE 10

Emulsion Without Emulsifier

The following oily phase is heated to 80° C.:

| | |
|---|---|
| jojoba oil | 4.0 g |
| polyisobutene | 4.0 g |
| octyl stearate | 4.0 g |
| oleyl acetate | 2.0 g |

The following aqueous phase is heated to 80° C.:

| | |
|---|---|
| glycerine 30° Codex | 3.0 g |
| carboxyvinyl polymer | 0.45 g |
| lubragel MS ® | 4.0 g |
| pure sodium hydroxide | 0.055 g |
| preservatives | 0.55 g |
| perfume | 0.20 g |
| demineralized water | 30.0 g |

The oily phase is dispersed in the aqueous phase under very gentle agitation and high shear for half an hour. The emulsion thus formed is cooled slowly to 45° C., then 3 grams of talc is added under strong agitation. When dispersion of the talc is complete, cooling is continued under slow agitation. When the temperature reaches 25° C., the following premixture is added under moderate agitation:

| | |
|---|---|
| demineralized water | 30 g |
| suspension of ribosomes | 0.05 g |

Then, under the same agitation, 0.2 g of perfume is added.

EXAMPLE 11

An oil-in-water emulsion is prepared in the following manner:

The components of the following oily phase are heated to 80° C.:

| | |
|---|---|
| self-emulsifiable glycerol stearate (arlacel 165 ® from ICI) | 6 g |
| cetyl alcohol | 1 g |
| ethoxylated soya sterol (generol 122 E 10 ® from Henkel) | 2 g |
| mixture of vaseline oil and lanolin alcohol (Amerchol L101 ® from the Amerchol Co.) | 3 g |
| petrolatum and lanolin alcohol (Amerchol CAB ® from the Amerchol Co.) | 1 g |

-continued

| | |
|---|---|
| safflower oil | 6 g |
| karite butter | 3 g |
| propylparaben | 0.05 g |

The following aqueous phase is prepared which is also heated to 80° C.:

| | |
|---|---|
| demineralized water | 60 g |
| 70% sorbitol | 3 g |
| xanthan gum | 0.3 g |
| methylparaben | 0.1 g |

When the xanthan gum is well dispersed, the oily phase is added to the aqueous phase at 80° C., and vigorous agitation is carried out for 20 minutes. The emulsion forms. Then the agitation is reduced and the emulsion is slowly cooled to 40° C. Next 2 g of water containing 0.15 g of imidazolidinyl urea, followed by 0.3 g of perfume, is added to the emulsion. 0.5 g of the suspension of ribosomes is also added at this temperature.

Study of the evaluation of the "stimulating" and "regenerating" action of the ribosomes according to the invention on the keratinocytes of the human epidermis.

In vitro methods allow the rapid evaluation of the activity of synthetic and natural products. They are put directly in contact with their target, the cells of the dermis or epidermis.

a) Substances

The active product studied is the product of Example 1, the suspension of ribosomes.

Leucine (labeling with $^{14}C$ of all the carbons, specific activity 11.7 GBq/mmole), and thymidine (labeling with tritium on the carbon in position 6, specific activity 1.07 TBq/mmole) were provided by Amersham.

All the culture reagents, media, and additives were provided by commercial companies such as MERCK and GIBCO. CMA=Culture Medium for Attachment of the keratinocytes, MEM/199 medium (75/25% v/v; GIBCO) having added to it 50 IU/ml of penicillin, 50 µg/ml of streptomycin, 10% of fetal calf serum, 10 ng/ml of choleric toxin, 5 µg/ml of bovine insulin, 0.4 µg/ml of hydrocortisone, 5 µg/ml of choline, and 8.5 µg/ml of inositol.

CMI=Culture Medium for Incubation in the presence of compounds, that is CMA medium without EGF or fetal Calf Serum (FCS).

The medium used for the labeling of the proteins with $^{14}C$ leucine and of the DNA with $^3H$ thymidine is MEM medium without leucine (BIOPREDIC) having added to it 50 IU/ml of penicillin, 50 µg/ml of streptomycin, 6.3 $10^{-7}$ M of radiolabeled leucine (7.4 kBq/ml) and 3.4 $10^{-8}$ M of tritiated thymidine (37 kBq/ml).

b) Experimental Method

The active product was filtered, and then added to the CMI medium at concentrations of 0.01% and 0.1% (v/v). The removal of skin was carried out according to the recommendations of the National Ethics Committee on a 73-year old woman ("post mortem"). The keratinocytes were obtained by dissociation of the epidermis with trypsin.

The cells, of mammary origin, were used after the 3rd passage. They were seeded in 96-well culture plates, at the rate of $7 \times 10^4$ cells per well in 0.1 ml of CMA. They were cultured for one day and used before confluence.

The active product was put in the presence of the cells for 20 hours. Each experiment carried out was in triplicate. Control cultures were tested in the same way, but in the absence of the produce being tested, either in CMI medium (control culture), or in CMA medium (positive control culture).

For the incorporation of radiolabeled leucine and thymidine, the keratinocytes were incubated with leucine radiolabeled with and tritiated thymidine for 4 hours. The cellular covering was washed in order to eliminate the non-incorporated precursors and then counted by liquid scintillation. The values were expressed in dpm/culture well.

c) Results:

The tests were carried out at two concentrations of the active product, 0.01 to 0.1% (v/v), under conventional conditions, i.e. under cultures carried out on a flat plastic support. The effects of the compound were evaluated by measuring two functional parameters, neosynthesis of the proteins and neosynthesis of DNA, after 20 hours of incubation. The fetal calf serum (FCS) and the epidermal growth factor (EGF) were removed from the incubation medium to make it easier to reveal cell stimulation. The effect of the addition of FCS and EGF in the culture medium (positive control) was studied in the same way.

Neosynthesis of the Proteins

The active product significantly increases this parameter at the two concentrations studied. The maximum effect, +274% relative to the control cultures, is obtained with the weakest concentration; it was comparable to that observed with the positive control (Table 1, FIG. 1).

Incorporation of the Thymidine in the DNA

Figure 2:
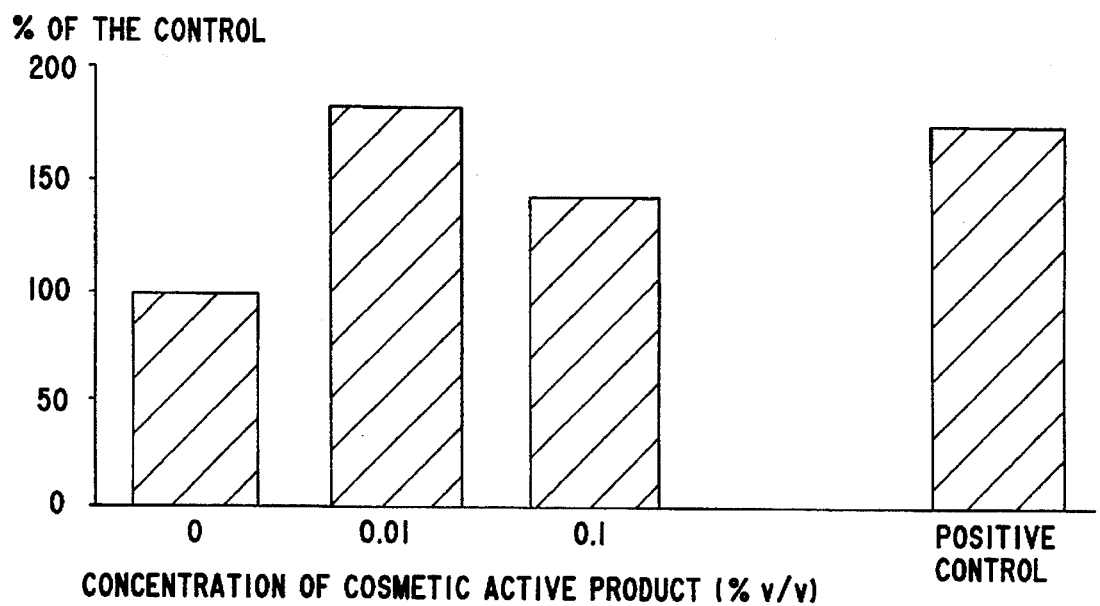
FIG. 2 is a bar graph, similar to that of FIG. 1, showing the results of the tests of incorporation of thymidine in the DNA.

The active product also significantly increases this parameter at the two concentrations studied. The maximum effect, +82% relative to the control cultures, was obtained with the weakest concentration; it was similar to that observed for the positive control (Table 1, FIG. 2).

These results show that, under the experimental conditions, the active product exerted a significant stimulating effect vis-a-vis human keratinocytes, this cytostimulating action being at its maximum at the weaker concentration tested, 0.01% (v/v).

TABLE 1

Incorporation of ($^{14}C$)-leucine in the proteins and of ($^3H$)-thymidine in the DNA of keratinocytes in culture incubated for 20 hours in the presence of the active product

| Parameter | Active Product Concentration (%, v/v) | | | Positive control |
|---|---|---|---|---|
| | 0 | 0.01 | 0.1 | |
| Neosynthesis of the proteins | 1123 | 4726 | 3804 | 4167 |
| | 1107 | 4391 | 2743 | 3721 |
| | 1396 | 4450 | 3111 | 3526 |
| | 1209 | 4522* | 3219* | 3805* |
| | +/− | +/− | +/− | +/− |
| | 3.62 | 179 | 539 | 329 |
| | (100) | (374) | (266) | (315) |
| Neosynthesis of DNA | 1254 | 2689 | 1993 | 2253 |
| | 1243 | 2043 | 1846 | 2274 |
| | 1504 | 2561 | 1869 | 2528 |
| | 1334 | 2431* | 1903* | 2352* |
| | +/− | +/− | +/− | +/− |
| | 148 | 342 | 79 | 153 |
| | (100) | (182) | (143) | (176) |

The results are expressed in dpm/culture well.
Characters in bold: average and standard deviation.
Between ( ): percentage relative to the control cultures.
*Average of the different groups of the control group (p < 0.05).

We claim:

1. A composition for skin care containing 0.00005% to 1.0% by weight of a suspension of ribosomes extracted from gram negative bacteria, and a cosmetic or dermatologically acceptable excipient.

2. The composition of claim 1 wherein said gram negative bacteria are selected from the group consisting of Klebsiella pneumoniae, Hafnia, and *Escherichia coli*.

3. The composition of claim 2 wherein said bacteria are Klebsiella pneumoniae deposited at Pasteur Institute in Paris, France under number I-163.

4. The composition of claim 2 wherein said bacteria are Hafnia deposited at Pasteur Institute in Paris, France under number I-868.

5. The composition of claim 2 wherein said bacteria are *Escherichia coli* deposited at Pasteur institute in Paris, France under number I-870.

6. The composition of claim 1 containing 0.005% to 0.05% by weight of a suspension of said ribosomes extracted from said microorganisms.

7. The composition of claim 6 containing about 0.01% of said suspension of said ribosomes.

8. The composition of claim 1 wherein said ribosomes are produced by the process comprising culturing said gram negative bacteria on a solid or liquid culture medium;

isolating said cultured bacteria;

lysis of said isolated bacteria to form a lysate; and subjecting said lysate to centrifugation.

9. The composition of claim 8, wherein the centrifuged lysate is subjected to a precipitation with ammonium sulfate followed by centrifugation to form a precipitate.

10. The composition of claim 9, wherein said precipitate is subjected to a molecular sieve, subjected to precipitation with PEG 6000 followed by centrifugation and subjected to dialysis.

11. The composition of a claim 1, wherein said excipient is dermatologically acceptable and wherein said composition additionally comprises at least one additive selected from the group consisting of oleyl acetate, titrated dry extract from Centella Asiatica, evening primrose oil and amino acids.

12. The composition of claim 1 wherein said excipient is acceptable for use on human faces, necks and hands.

13. A method of treating human skin comprising applying the composition of claim 1 to said human skin.

14. The method of claim 13 wherein the gram negative bacteria are selected from the group consisting of Klebsiella pneumoniae, Hafnia, and *Escherichia coli*.

* * * * *